United States Patent
Zasloff

(10) Patent No.: US 9,931,287 B2
(45) Date of Patent: Apr. 3, 2018

(54) SIMPLE MICRO-PARTICULATE SUSPENSION OF BEHENTRIMONIUM CHLORIDE WITH FAVORABLE DISTRIBUTIVE AND ADSORPTIVE PROPERTIES

(71) Applicant: Formula XO, Inc., Arlington, VA (US)

(72) Inventor: Michael Zasloff, Merion, PA (US)

(73) Assignee: FORMULA XO, INC., Arlington, VA (US)

( * ) Notice: Subject to any disclaimer, the term of this patent is extended or adjusted under 35 U.S.C. 154(b) by 0 days.

(21) Appl. No.: 14/289,729

(22) Filed: May 29, 2014

(65) Prior Publication Data

US 2014/0356400 A1    Dec. 4, 2014

Related U.S. Application Data

(60) Provisional application No. 61/830,410, filed on Jun. 3, 2013.

(51) Int. Cl.
| | |
|---|---|
| *A61Q 5/02* | (2006.01) |
| *A61K 8/45* | (2006.01) |
| *A61Q 5/12* | (2006.01) |
| *A61K 8/41* | (2006.01) |
| *A61K 8/02* | (2006.01) |

(52) U.S. Cl.
CPC ............ *A61K 8/416* (2013.01); *A61K 8/0275* (2013.01); *A61K 8/45* (2013.01); *A61Q 5/02* (2013.01); *A61Q 5/12* (2013.01); *A61K 2800/412* (2013.01)

(58) Field of Classification Search
None
See application file for complete search history.

(56) References Cited

U.S. PATENT DOCUMENTS

| | | |
|---|---|---|
| 6,312,675 B1 | 11/2001 | Deane |
| 8,349,301 B2 | 1/2013 | Wells et al. |
| 2004/0052748 A1 | 3/2004 | Vondruska |
| 2006/0292086 A1 | 12/2006 | Curtis |
| 2012/0021025 A1 | 1/2012 | Bendejacq et al. |

OTHER PUBLICATIONS

International Search Report and Written Opinion issued by the U.S. Patent and Trademark Office as International Searching Authority for International Application No. PCT/US2014/039921 dated Oct. 9, 2014 (9 pgs.).

*Primary Examiner* — David J Blanchard
*Assistant Examiner* — Sarah J Chickos
(74) *Attorney, Agent, or Firm* — Wilmer Cutler Pickering Hale and Dorr LLP

(57) ABSTRACT

A personal care composition for hair and skin applications includes an aqueous solution consisting essentially of aggregates of behentrimonium chloride and dihydroxypropyl PEG-5 linoleammonium chloride. The composition forms micro particles or aggregates of behentrimonium chloride that exhibits surprising distributive properties in aqueous solution of a nature beneficial to its application to hair or skin surfaces.

14 Claims, 4 Drawing Sheets

MOLECULAR DISTRIBUTION IN SOLUTION OF BC

AGGREGATES OF BC MICELLES

BC AND DPLC IN WATER SOLUTION

BC MICELLES

BC ALONE IN WATER SOLUTION

SIMPLE MICRO-PARTICULATE SUSPENSION OF BEHENTRIMONIUM CHLORIDE WITH FAVORABLE DISTRIBUTIVE AND ADSORPTIVE PROPERTIES

CROSS REFERENCE TO RELATED APPLICATIONS

This application claims the benefit of priority under 35 U.S.C. § 119(e) to U.S. Provisional Application No. 61/830,410 filed Jun. 3, 2013, entitled "A Simple Micro-Particulate Suspension of Behentrimonium Chloride with Favorable Distributive and Adsorptive Pproperties", the contents of which are hereby incorporated by reference in their entirety.

FIELD OF THE INVENTION

This invention relates to compositions containing and methods of formulating behentrimonium chloride hair and skin applications.

BACKGROUND OF THE INVENTION

Behentrimonium chloride (N,N,N-trimethyldocosan-1-aminium chloride; CAS# 17301-53-0), a compound commonly found in cosmetics such as conditioners, shampoos, and also in household detergents, has the structure shown in 1.

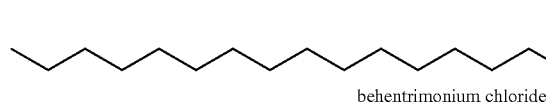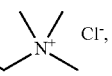

behentrimonium chloride

Behentrimonium chloride is widely used in hair products because of its potent conditioning antistatic and detangling properties, its ability to restore and rebuild damaged hair, its softening effects, and its antimicrobial properties.

Behentrimonium chloride is a waxy compound that is generally solubilized in hot water (85° C.). It is used at concentrations between 0.5-3 wt %. At room temperature an aqueous solution of behentrimonium chloride clouds, forming micelles, as would be expected of a cationic long chain alkyl compound. The solution is uniformly cloudy, and becomes increasingly more so as the concentration of behentrimonium chloride increases. Dilution of a concentrated aqueous dispersion of behentrimonium chloride creates a less dilute but homogeneous dispersion of the compound.

Behentrimonium chloride is believed to achieve its beneficial effects on hair in part through its penetration into the hair shaft. Penetration is dependent on the local concentration of behentrimonium chloride on the hair shaft surface. In the application of a product to wet hair, as in the application of a conditioner following the use of a shampoo, dilution on the surface of hair is naturally expected to occur. As the beneficial effect of a compound is dependent on the surface concentration of the compound, then its dilution on the hair surface reduces its efficacy, since diffusion into the hair shaft is a concentration-dependent process.

This could be solved in part by raising the concentration of behentrimonium chloride in the formulation to account for surface dilution. However, in the case of behentrimonium chloride at high concentrations (>7%) the solution becomes viscous, waxy, and solidifies on storage. In addition, as larger amounts of behentrimonium chloride are applied to the hair surface the hair becomes waxy and stiff.

Current hair conditioning formulations that utilize behentrimonium chloride include it as a minor component in a complex mixture that generally includes emulsifying aides such as medium chain fatty alcohols, such as cetyl alcohol, emulsifying wax and silicones, such as dimethicone. These formulations are designed to create a homogenous stable emulsion that coats the hair with a combination of substances, including a low concentration of behentrimonium chloride, that together create the desired effects. While meeting with some success in improving the stability of behentrimonium chloride-containing emulsions, the conditioners are generally oily and deposit an oily residue on the hair.

SUMMARY OF THE INVENTION

Simple compositions containing behentrimonium chloride for the purpose of its use on hair and skin surfaces are described. The compositions include behentrimonium chloride with a second compound, dihydroxypropyl PEG-5 linoleammonium chloride, to achieve a simple formulation of micro particles or aggregates of behentrimonium chloride that exhibits surprising distributive properties in aqueous solution of a nature beneficial to its application to hair or skin surfaces.

The composition includes an amount of behentrimonium chloride with dihydroxypropyl PEG-5 linoleammonium chloride in such a proportion that behentrimonium chloride forms stable micro-aggregates in aqueous solution at temperatures below 50° C.

In one embodiment, the micro-aggregate suspension includes only two components in addition to water, behentrimonium chloride and dihydroxypropyl PEG-5 linoleammonium chloride.

In yet another embodiment of the invention, the formulation includes other components required to exhibit certain properties, such as fragrances or colorants. In certain embodiments, the micro-aggregate composition otherwise lacks additional emulsifying, surfactant or other surface active agents that typically are used to provide the penetration properties of conventional behentrimonium chloride-containing compositions.

In certain embodiments, the micro-aggregate suspension contains behentrimonium chloride at a concentration between 0.5 wt % and 10 wt % and dihydroxypropyl PEG-5 linoleammonium chloride between 0.5 wt % and 30 wt %, with the weight ratio of the two compounds about 1:1. In one embodiment, the weight proportions of behentrimonium chloride to dihydroxypropyl PEG-5 linoleammonium chloride are about 1:1 and the concentration of behentrimonium chloride is about 6-7%.

The composition can be applied by spray or direct manual application to the hair.

The micro-aggregate suspension according to one or more embodiments provides a superior degree of hair conditioning than can be achieved using behentrimonium chloride alone, or in combination with the usual multi-component compositions utilized in commercial hair conditioners.

BRIEF DESCRIPTION OF THE INVENTION

Both the foregoing summary of the invention and the following detailed description of the invention are exemplary and explanatory and are intended to provide further details of the invention as claimed. Other objects, advantages, and novel features will be readily apparent to those skilled in the art from the following detailed description of the invention.

DETAILED DESCRIPTION OF THE INVENTION

Figure 1A:
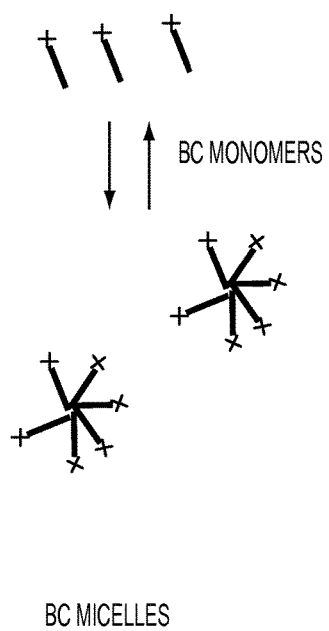
FIGS. 1A and 1B are schematic illustrations depicting complex macromolecular structures formed by FIG. 1A behentrimonium chloride alone and FIG. 1B by a combination of behentrimonium chloride and dihydroxypropyl PEG-5 linoleammonium chloride in water according to one or more embodiment.

Compositions containing and a simple method of formulating behentrimonium chloride for the purpose of its use on hair and skin surfaces are disclosed. Behentrimonium chloride is a long chain fatty acid derivative that can penetrate the superficial layers of skin and the shafts of hair. Penetration into skin and hair achieves the maximal desired benefits of this compound, those being its restoration of the hydrophobic composition of these tissues, and the neutralization of the negative zeta potential within the matrices of hair and superficial keratinocytes. Penetration is a concentration dependent process: the higher the local concentration of behentrimonium chloride in the immediate surfaces of skin and hair, the greater the numbers of these molecules that will penetrate.

In one aspect, personal care compositions that provide high local concentrations of behentrimonium chloride at the point of application utilizing a dilute solution of behentrimonium chloride are provided.

In another aspect, a method for making personal care compositions that provide high local concentrations of behentrimonium chloride utilizing a dilute solution of behentrimonium chloride includes combining behentrimonium chloride with dihydroxypropyl PEG-5 linoleammonium chloride 2 in such a proportion that behentrimonium chloride forms stable micro-aggregates in aqueous solution at temperatures below 50° C. The structure of dihydroxypropyl PEG-5 linoleammonium chloride 2 is shown below.

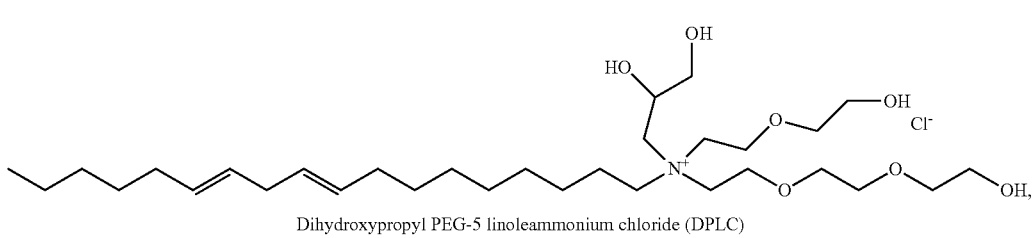

Dihydroxypropyl PEG-5 linoleammonium chloride (DPLC)

It has been surprisingly discovered that the combination of a solution of behentrimonium chloride with dihydroxypropyl PEG-5 linoleammonium chloride in the absence of other fatty acids, detergents, and surfactants or other additives that have been traditionally used to improve behentrimonium chloride penetration provides a stabilized microaggregate suspension that can provide desired penetrative properties. Addition of a solution of dihydroxypropyl PEG-5 linoleammonium chloride to a solution of results in the immediate aggregation of molecules of behentrimonium chloride, evidenced by the sudden increase in cloudiness or turbidity of the behentrimonium chloride solution.

In addition, it has been surprisingly discovered that hydroxypropyl PEG-5 linoleammonium chloride beneficially alters the solubility properties of behentrimonium chloride in water. As shown in the Examples below, dihydroxypropyl PEG-5 linoleammonium chloride causes a homogeneous dispersion of behentrimonium chloride to aggregate in solution; and for such aggregates to exhibit sufficient stability that they physically persist when diluted into water. Behentrimonium chloride is thus applied as dense micro-aggregates to the hair or skin surface rather than as a uniform solution. Microscopic "dollops" of behentrimonium chloride create high local surface concentrations that could otherwise not be reached with the concentration of behentrimonium chloride present at the overall concentration applied. The dilute solution of micro-aggregates can be easily sprayed on the surface of skin or hair and achieves an effect that is considerably more advantageous than previously known for behentrimonium chloride. Individuals on whom the formulation has been used report benefits that include outstanding silkiness of hair, softness, increased volume and enhanced moisture compared to existing products, and without a residual residue. In addition, the formulation eliminates the need for agents to enhance shine, provide moisture, and replace essential oils, all desired effects being provided by the micro-particulate dispersion of behentrimonium chloride.

Figure 2A:
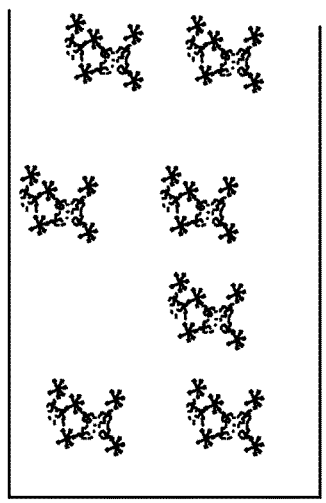
FIGS. 2A and 2B are schematic illustrations showing the molecular distribution of aggregates of FIG. 2A behentrimonium chloride and dihydroxypropyl PEG-5 linoleammonium chloride in water solution and FIG. 2B of behentrimonium chloride alone in water solution, according to one or more embodiment.

Behentrimonium chloride ("BC"), like other cationic lipids disperses in solution into micellar structures (FIGS. 1A and 2A). In contrast, dihydroxypropyl PEG-5 linoleammonium chloride ("DHLC") is a compound structurally unable to form micelles in water, due to the unsaturated alkyl chain, and the large polar substituents that are covalently linked to the nitrogen atom. DPLC, however, because of the numerous hydroxyl groups and its overall hydrophobic character will organize into loose networks stabilized by hydrogen bonds.

Figure 1B:
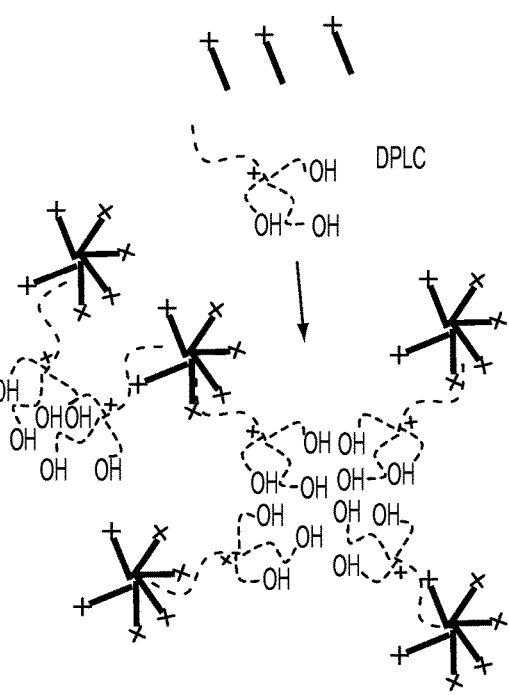
Figure 2B:
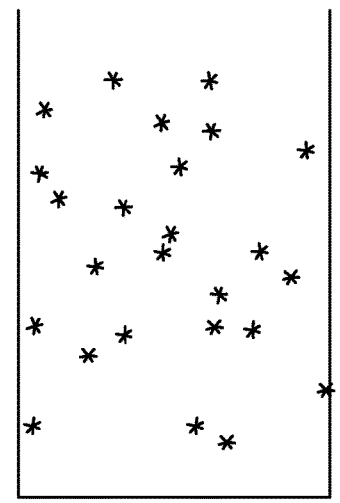

When behentrimonium chloride and dihydroxypropyl PEG-5 linoleammonium chloride are added together in solution the unsaturated alkyl group of DPLC intercalate within the micelles of BC (FIGS. 1B and 2B). The BC/DPLC structures begin to form micro-aggregates as evidenced by the increasing turbidity of the milky homogeneous BC solution upon addition of the clear solution of DPLC. Over the course of several hours the turbidity of the binary solution increases, reached a maximum with about 12 hours at room temperature. Micro-aggregation of BC occurs as the DPLC molecules that have inserted within the BC micelles interact with one another through hydrogen bonding resulting in the clustering of the mixed DPLC-BC micelles, thereby creating BC micelle aggregates (FIGS. 1A, 1B, 2A and 2B). These continue to grow through fusion of the BC micelles as a consequence of their physical proximity. The aggregates range in size from 1-100 microns, in a heterogeneous dispersion.

Figure 3:
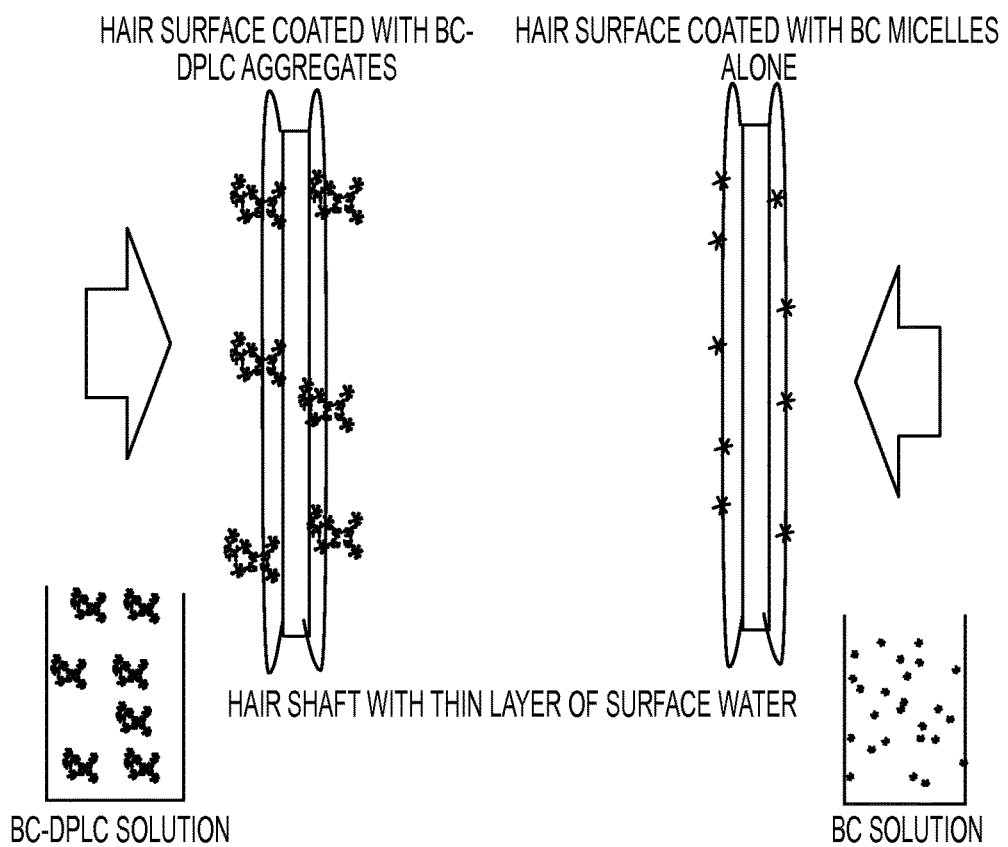
FIG. 3 is a schematic illustration of a micro-aggregate composition of behentrimonium chloride and dihydroxypropyl PEG-5 linoleammonium and a behentrimonium chloride micelle solution interacting with a hair shaft.

Applying a suspension of BC/DPLC aggregates onto the water film covering wet hair or skin distribute BC in aggregates rather than as individual BC monomers or micelles. FIG. 3 is a schematic illustration of a micro-aggregate composition made up of only BC and DPLC interacting with a hair shaft according to one or more embodiments and only BC micelles. Because BC forms an aggregate containing a high number of both BC and DPLC moelcules, each interaction of a micro-aggregate with the hair shaft provides a local high concentration of BC. The local concentration of BC on the hair shaft is increased in proportion to the difference in molar numbers of BC within the aggregate compared with the monomeric micelle. Thus, BC/DPLC deposits as zones of high BC concentration over the hair shaft, permitting higher local concentrations to accumulate within the hair shaft than will occur with an equal concentration of BC alone.

Figure 4:
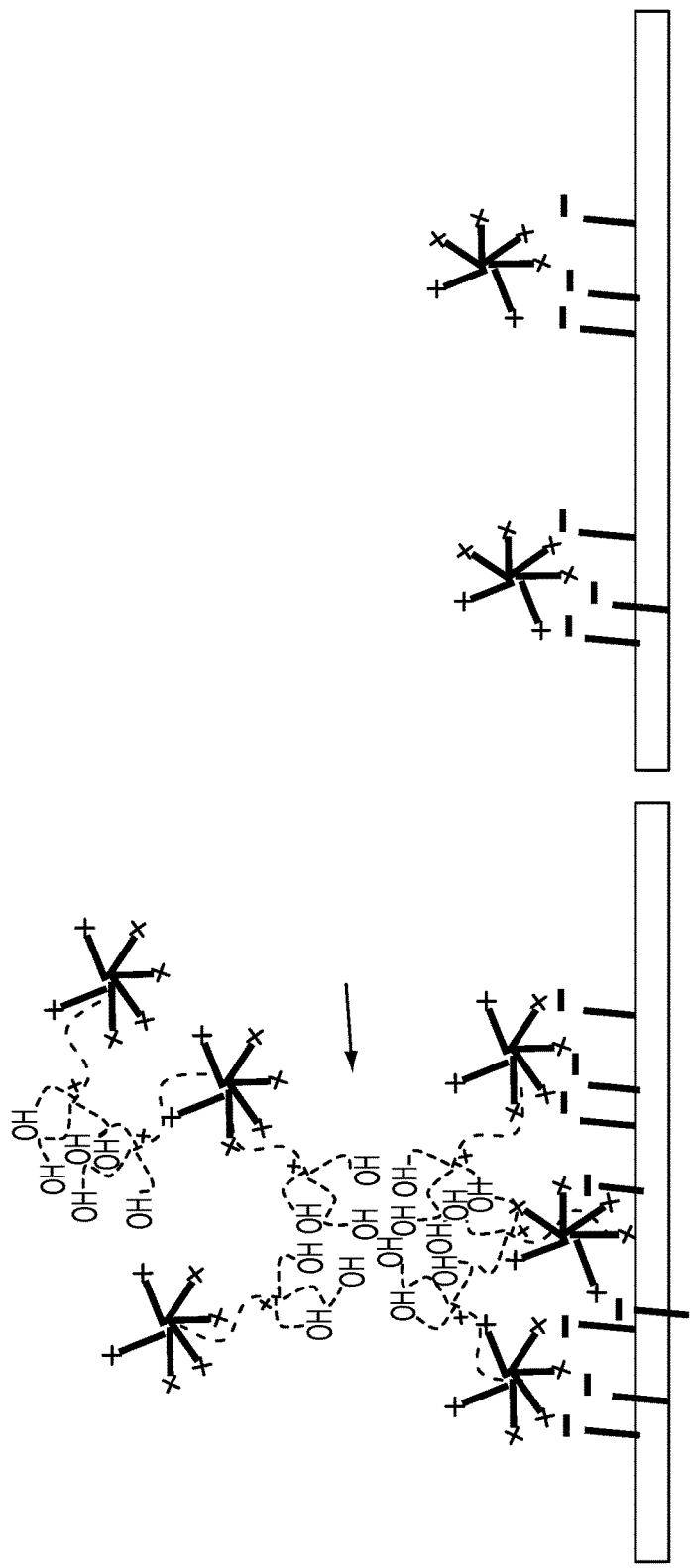
FIG. 4 is a schematic illustration showing improved adherence properties of a behentrimonium chloride and dihydroxypropyl PEG-5 linoleammonium chloride formulation on hair and negatively charged surfaces as compared to behentrimonium chloride alone according to one or more embodiments.

Because of the greater density of positive or cationic charge on each aggregate, the probability that an aggregate will attach electrostatically to a hair shaft, which naturally carries a net negative electrostatic charge, will be greater for the aggregate of BC micelles than for a single BC micelle as is illustrated schematically in FIG. 4. As such, the retentive or adherence properties of the aggregate is greater than that observed for a monomeric micelle.

The formation of BC micro aggregates in solution is inhibited by the presence of other synthetic ionic and neutral surfactants, detergents, and fatty acids. Thus, although several commercial hair care products utilize both BC and DPLC, they are included along with components, such as cetyl alcohol and silicone, that interfere with the formation of BC/DPLC aggregates. These commercial formulations create a single homogeneous viscous phase, rather than the desired suspension of visible micro-aggregates of BC disclosed in this invention.

EXAMPLES

Example 1

The purpose of this example is to demonstrate the effect of adding DPLC to a solution of BC on the state of aggregation of BC.

A solution of BC is prepared by adding 20 grams BTMC-85 (Mason chemical company, 80% active by weight) to 330 ml of water and heating to 85° C. 50 grams of DPLC (SL-5, Mason chemical company, 35% active by weight) is added. The solution is clear and a slight yellow in color. A solution of BC is prepared in water as above but without addition of DPLC. Both solutions are cooled to room temperature.

The BC/DPLC solution separates into two layers: a white milky upper layer, about ½ the volume of the solution, while the lower half remains clear. The BC solution forms a uniform milky suspension.

The two formulations are each mixed vigorously to disperse their contents and then sprayed onto the surface of a pan of water at room temperature (20° C.).

The BC/DPLC layer begins to aggregate on the surface; some settles down into the depth of the water layer, creating a turbid suspension. The BC suspension remains on the water surface and gradually diffuses down into the water layer resulting in a nearly clear, transparent solution.

This simple example demonstrates that DPLC will cause BC to aggregate and that the aggregates exhibit sufficiently stability at room temperature to withstand dilution in water.

The cloudy diluted suspension of BC/DPLC is then warmed from 20° C. When the temperature reached 38° C., the suspension clarified. This teaches us that the aggregates are unstable at temperatures close to body temperature. Thus, aggregates that deposit on wet hair would be expected to disassemble on the hair shaft.

Example 2

A BC/DPLC suspension is prepared as described in Example 1. To various portions, decyl glucoside, sodium lauryl sulfate, cocomidyl betaine, or sodium lauryl sarcosinate is added. Addition of any of these surfactants to their critical micelle concentration results in the dissolution of the desired BC/DPLC micro aggregates.

Example 3

A BC/DPLC suspension prepared as in Example 1 and a BC solution (at the same concentration) are sprayed on to a clear glass surface held perpendicular to the ground. The liquids run freely downward. The surface onto which the BC/DPLC suspension had been sprayed is covered with a multitude of retained particles of BC, while that sprayed with the BC solution is clear. This teaches that spraying of the BC/DPLC formulation achieves the desired benefit, as expected in its use on hair and skin.

Example 4

A suspension of BC/DPLC was prepared as described in Example 1. It was sprayed onto the wet hair of individuals and left on while the hair dried. The hair was combed and brushed while still damp.

The hair was noted to feel silky and soft with an excellent sheen and luster. It exhibited favorable anti-frizzing properties and could be styled easily. Those using the formulation felt their hair to feel light and with less residue than usual.

A solution of BC, equal in the concentration BC as in Example 1, was also sprayed on the wet hair of an individual, as described above. The hair was noted to feel oily, and lacked the feel and management properties of the BC/DPLC formulation of Example 1.

What is claimed is:

1. A personal care composition comprising;
    an aqueous suspension comprising actives consisting of micro-aggregates of behentrimonium chloride and dihydroxypropyl PEG-5 linoleammonium chloride,
    wherein the micro-aggregates are in the range of 1-100 µm, and
    wherein the composition is free of surfactants, emulsifiers, and surface active agents.

2. A personal care composition consisting of an aqueous suspension consisting of micro-aggregates of behentrimonium chloride and dihydroxypropyl PEG-5 linoleammonium chloride, wherein the behentrimonium chloride and the dihydroxypropyl PEG-5 linoleammonium chloride are present in such a proportion to provide stable micro-aggregates in aqueous solution.

3. The personal care composition of claim 1 or 2, wherein the composition contains behentrimonium chloride at a concentration between 0.5 wt % and 10 wt % and dihydroxypropyl PEG-5 linoleammonium chloride between 0.5 wt % and 30 wt %.

4. The composition of claim 3, wherein the weight ratio of the two compounds is about 1:1.

5. The composition of claim 4, wherein the aggregates are stable up to a temperature of 50° C.

6. The personal care composition of claim 1, wherein the composition is a hair care composition.

7. A method of preparing a personal care composition comprising:
    combining actives consisting of behentrimonium chloride and dihydroxypropyl PEG-5 linoleammonium chloride in an aqueous solvent to provide micro-aggregates in the range of 1-100 µm, wherein the composition is free of surfactants, emulsifiers and surface active agents.

8. The method of claim 7, wherein the proportions of behentrimonium chloride and dihydroxypropyl PEG-5 linoleammonium chloride are such that the resulting solution separates into two-phases at room temperature, with the upper phase comprised of aggregated behentrimonium chloride.

9. The method of claim 7 where the weight proportions of behentrimonium chloride to dihydroxypropyl PEG-5 linoleammonium chloride are about 1:1 and where the concentration of behentrimonium chloride is about 6-7%.

10. The method of claim 7, where other components are added to provide additional necessary properties of the intended application, such as fragrances, colorants, preservatives.

11. The method of claim 10, wherein the additional the agents are mixed
    (a) concomitantly;
    (b) as an admixture;
    (c) separately and simultaneously or concurrently; or
    (d) separately and sequentially.

12. A method of using a personal care product comprising providing a composition according to claim 1; and applying the composition to the hair or skin.

13. The method of claim 12 where the composition is used as a "leave on" product, used without subsequent removal by washing from the hair or skin.

14. A personal care composition consisting of an aqueous suspension consisting of micro-aggregates of behentrimonium chloride and dihydroxypropyl PEG-5 linoleammonium chloride, and one or more of a fragrance, colorant and preservative, wherein the behentrimonium chloride is present at a concentration between 0.5 wt % and 10 wt % and dihydroxypropyl PEG-5 linoleammonium chloride is present at a concentration between 0.5 wt % and 30 wt %.

* * * * *